(12) United States Patent
Burkholz et al.

(10) Patent No.: US 12,599,750 B2
(45) Date of Patent: Apr. 14, 2026

(54) VASCULAR ACCESS CONNECTOR SUPPORT DEVICE, SYSTEMS, AND METHODS

(71) Applicant: Becton, Dickinson and Company, Franklin Lakes, NJ (US)

(72) Inventors: Jonathan Karl Burkholz, Salt Lake City, UT (US); Curtis H. Blanchard, Riverton, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/956,580

(22) Filed: Sep. 29, 2022

(65) Prior Publication Data

US 2023/0012763 A1      Jan. 19, 2023

Related U.S. Application Data

(62) Division of application No. 16/716,142, filed on Dec. 16, 2019, now Pat. No. 11,497,891.

(60) Provisional application No. 62/786,732, filed on Dec. 31, 2018.

(51) Int. Cl.
*A61M 25/02*          (2006.01)

(52) U.S. Cl.
CPC ..... *A61M 25/02* (2013.01); *A61M 2025/0266* (2013.01); *A61M 2025/028* (2013.01)

(58) Field of Classification Search
CPC ............ A61M 2025/028; A61M 25/02; A61M 2209/088
See application file for complete search history.

(56) References Cited

U.S. PATENT DOCUMENTS

| | | | | |
|---|---|---|---|---|
| 4,250,880 | A  * | 2/1981 | Gordon ................. | A61M 25/02 128/DIG. 26 |
| 6,231,547 | B1 | 5/2001 | O'Hara | |
| 9,056,186 | B2 | 6/2015 | Wright et al. | |
| 2006/0270994 | A1* | 11/2006 | Bierman ............... | A61M 25/02 604/180 |
| 2012/0041377 | A1* | 2/2012 | Haak ..................... | A61M 25/02 604/180 |
| 2012/0197204 | A1 | 8/2012 | Helm, Jr. | |
| 2012/0271239 | A1 | 10/2012 | Andino et al. | |
| 2013/0345639 | A1* | 12/2013 | Spittler ................. | A61M 25/02 604/180 |
| 2018/0344983 | A1 | 12/2018 | Funk et al. | |

FOREIGN PATENT DOCUMENTS

| | | | |
|---|---|---|---|
| WO | 2013090903 A1 | 6/2013 | |
| WO | 2017042359 A1 | 3/2017 | |
| WO | 2019204413 A2 | 10/2019 | |
| WO | 2020055582 A1 | 3/2020 | |

* cited by examiner

*Primary Examiner* — Emily L Schmidt
(74) *Attorney, Agent, or Firm* — Kirton McConkie; Whitney Blair; Kevin Stinger

(57) ABSTRACT

A catheter system may include a catheter adapter, which may include a distal end, a proximal end, and a lumen extending through the distal end and the proximal end. The catheter system may include a connector coupled to the proximal end of the catheter adapter. The connector may include a T-connector. The catheter system may include a connector support device, which may be wedge-shaped to support the connector at an insertion angle.

3 Claims, 16 Drawing Sheets

VASCULAR ACCESS CONNECTOR SUPPORT DEVICE, SYSTEMS, AND METHODS

RELATED APPLICATIONS

This application is a divisional of U.S. patent application Ser. No. 16/716,142, filed on Dec. 16, 2019, and entitled VASCULAR ACCESS CONNECTOR SUPPORT DEVICE, SYSTEMS, AND METHODS, which claims the benefit of U.S. Provisional Patent Application No. 62/786,732, filed Dec. 31, 2018, and entitled VASCULAR ACCESS CONNECTOR SUPPORT DEVICE, SYSTEMS, AND METHODS, which are incorporated herein in their entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow insertion angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion.

Placement of the PIVC within the vasculature is essential for blood withdrawal and fluid infusion and yet may be difficult to maintain. Patients often want or need to have a normal range of body motion while the PIVC is inserted. Also, external objects may apply external forces to the PIVC and thereby shift the PIVC's location within the vasculature. In some instances, the external forces may cause back-and-forth dynamic movement of a tip of the PIVC or a static shift in the tip from its location within the vasculature.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems and methods. In some embodiments, a catheter system may include a catheter assembly, which may include a catheter adapter and a catheter. In some embodiments, the catheter adapter may include a distal end, a proximal end, and a lumen extending through the distal end and the proximal end. In some embodiments, the catheter may extend distally from the distal end of the catheter adapter. In some embodiments, the catheter may include a peripheral intravenous catheter (PIVC) or another suitable catheter. In some embodiments, the catheter adapter may be non-integrated, without an integrated extension tube extending from a side port.

In some embodiments, the catheter system may include a connector, which may be coupled to the proximal end of the catheter adapter. In some embodiments, the connector may include a T-connector or another suitable connector. In some embodiments, the T-connector may include a body, which may include a distal end and a proximal end. In some embodiments, the T-connector may include a side port extending from the body.

In some embodiments, in order to place the catheter within a blood vessel of a patient for fluid infusion and/or blood withdrawal, an introducer needle and the catheter may be inserted into skin of the patient at an insertion angle with respect to the skin. In some embodiments, the insertion angle may be about 30° or less. In some embodiments, the catheter system may include a connector support device, which may be wedge-shaped to support the connector at the insertion angle.

In some embodiments, the connector support device may facilitate stabilization of the connector and insertion of an instrument through the connector and catheter. In some embodiments, the instrument may include a probe (which may include a sensor), a light tube for disinfection, or another suitable instrument. In some embodiments, the instrument may include another catheter and may be used for blood withdrawal from the patient and/or infusion of fluid into the patient. In some embodiments, an instrument delivery device may be coupled to the proximal end of the connector, and the instrument may be advanced distally through the connector and into the catheter. In some embodiments, the instrument may be advanced distally beyond the catheter into the blood vessel of the patient.

In some embodiments, the connector and the catheter adapter may provide a straight pathway through which the instrument may travel and extend. In further detail, in some embodiments, a lumen of the connector may be axially aligned with the lumen of the catheter adapter. In some embodiments, the connector and connector support device may act as an extension set, which is removed to a degree from the patient to prevent disruption of the catheter insertion site. However, in some embodiments, a length of the connector and the catheter adapter may not be overly extended to facilitate an increased reach of the instrument. In some embodiments, a blood collection or fluid infusion device may be coupled to the proximal end of the connector.

In some embodiments, the connector support device may include an H-shape, which may include four leg portions and a bridge portion. In some embodiments, the H-shape may provide stabilization of the connector and the catheter assembly by preventing rocking from side to side. In some embodiments, the connector support device may include an upper surface, which may contact and support the connector. In some embodiments, the body and the side port of the T-connector may rest on the upper surface. In some embodiments, the connector support device may include a bottom surface configured to contact the skin of the patient.

In some embodiments, the connector support device may include various stabilization features. In some embodiments, the connector support device may include a ring or partial ring, which may extend from the upper surface. In some embodiments, the connector may extend through the ring or the partial ring. In some embodiments, the body of the T-connector may extend through the ring or the partial ring.

In some embodiments, the side port of the T-connector may extend through the ring or the partial ring.

In some embodiments, the upper surface may include a groove, which may be aligned with a longitudinal axis of the connector. In some embodiments, the connector may rest within the groove. In some embodiments, the upper surface may include another groove, which may be generally perpendicular to the longitudinal axis of the connector. In some embodiments, the side port of the T-connector may be configured to rest within the other groove.

In some embodiments, the upper surface of the connector support device may include one or more protrusions, which may be configured to contact the side port of the T-connector. In some embodiments, the protrusions may be disposed proximal and/or distal to the side port. In some embodiments, the protrusions may be disposed laterally to the ring or the partial ring.

In some embodiments, the connector support device may include a stepped surface forming an upper step and a lower step. In some embodiments, the upper step may include the groove. In some embodiments, the distal end of the body may include a luer adapter, which may rest within the lower step. In some embodiments, the lower step may be curved. In some embodiments, the lower step may be curved to match a cylindrical shape of the luer adapter. In some embodiments, a diameter of a curve of the lower step may be greater than a diameter of a curve of the groove. In some embodiments, the connector support device may include an extension, which may extend distally from the lower step. In some embodiments, the luer adapter may rest on the extension.

In some embodiments, the connector support device and the connector may be packaged with the connector support device pre-attached to the connector, which may prevent assembly by the clinician. Thus, in some embodiments, the connector support device may be coupled to the connector prior to insertion of the catheter and introducer needle into the blood vessel of the patient. In some embodiments, coupling of the connector support device to the connector post-insertion by the clinician is avoided.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
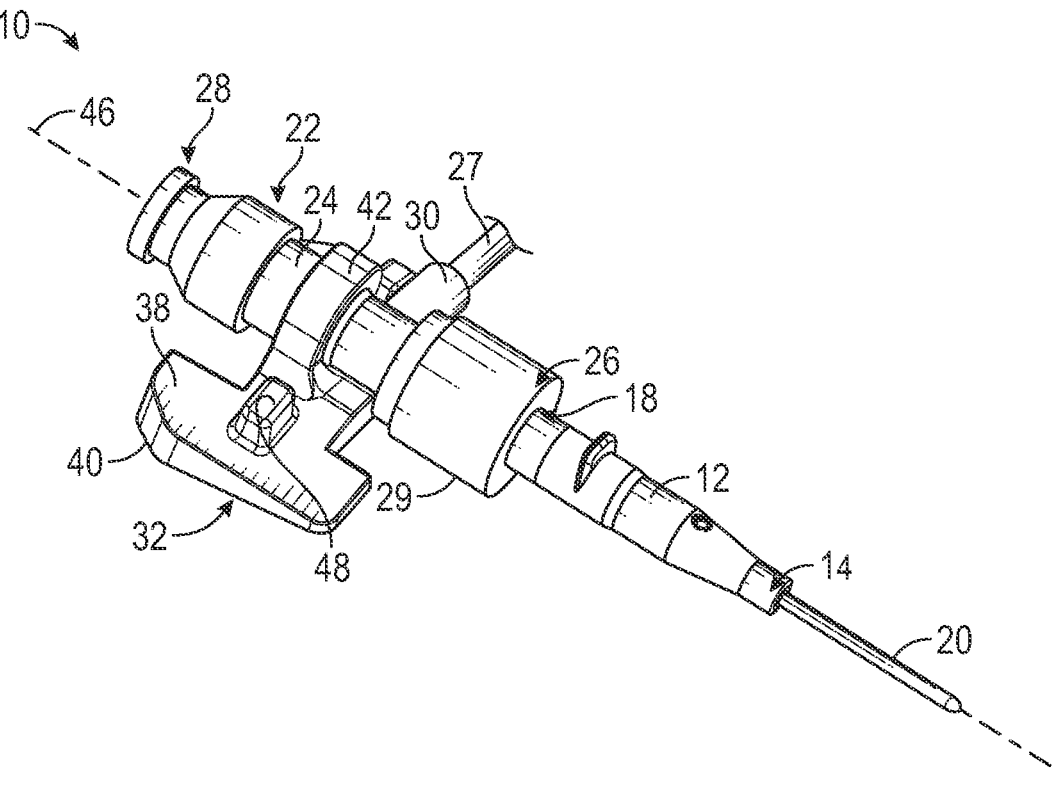
FIG. 1A is an upper perspective view of an example catheter system, illustrating an example connector and connector support device, according to some embodiments.
Figure 1B:
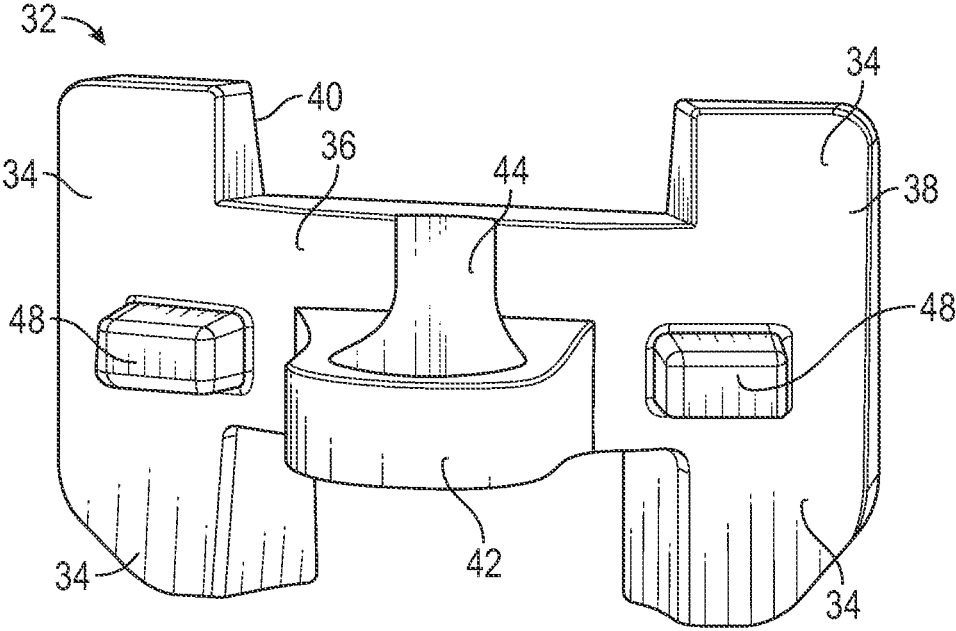
FIG. 1B is an upper perspective view of the connector support device of FIG. 1A, according to some embodiments.

Referring now to FIGS. 1A-1B, in some embodiments, a catheter system 10 may include a catheter adapter 12, which may include a distal end 14, a proximal end 18, and a lumen extending through the distal end 14 and the proximal end 18. In some embodiments, the catheter system 10 may include a catheter 20, which may extend distally from the distal end 14 of the catheter adapter 12. In some embodiments, the catheter 20 may include a peripheral intravenous catheter (PIVC) or another suitable catheter.

In some embodiments, the catheter adapter 12 may be non-integrated, without an integrated extension tube extending from a side port of the catheter adapter 12. In some embodiments, the catheter adapter 12 may be integrated, having an integrated extension tube extending from a side port of the catheter adapter 12. In some embodiments, catheter adapter 12 may include a single-use or multi-use blood control septum.

In some embodiments, the catheter system 10 may include a connector 22, which may be coupled to the proximal end 18 of the catheter adapter 12. In some embodiments, the connector 22 may include a body 24, which may include a distal end 26 and a proximal end 28.

In some embodiments, the distal end 26 of the body 24 may include a luer adapter 29, such as a male or female luer adapter. In some embodiments, the luer adapter 29 may include a slip or thread luer adapter. In some embodiments, the proximal end 28 of the body 24 may include another luer adapter 31, such as a male or female luer adapter. In some embodiments, the other luer adapter 31 may include a slip or thread luer adapter. In some embodiments, a septum may be disposed within the connector 22.

In some embodiments, the connector 22 may include a T-connector, as illustrated, for example, in FIG. 1A, or another suitable connector. In these and other embodiments, the connector 22 may include a side port 30 extending from the body 24. In some embodiments, the side port 30 may be in fluid communication with a lumen of the connector 22 extending through the distal end 26 and the proximal end 28. In some embodiments, an extension tube 27 may extend from the side port 30.

In some embodiments, in order to place the catheter 20 within a blood vessel of a patient for fluid infusion and/or blood withdrawal, an introducer needle (not illustrated) and the catheter 20 may be inserted into skin of the patient at an insertion angle with respect to the skin. In some embodiments, the insertion angle may be about 30° or less. In some embodiments, the insertion angle may be between 0° and 40°. In some embodiments, the catheter system 10 may include a connector support device 32, which may be wedge-shaped to support the connector 22 at the insertion angle. In further detail, a thickness of the connector support device 32 may increase in a distal to proximal direction.

In some embodiments, the connector support device 32 may facilitate stabilization of the connector 22 and insertion of an instrument (not illustrated) through the connector 22 and catheter 20. In some embodiments, the instrument may include a probe (which may include a sensor), a light tube for disinfection, or another suitable instrument. In some embodiments, the instrument may include another catheter and may be used for blood withdrawal from the patient and/or infusion of fluid into the patient. In some embodiments, an instrument delivery device may be coupled to the proximal end 28 of the connector 22, and the instrument may be advanced distally through the connector 22 and into the catheter 20. In some embodiments, the instrument may be advanced distally beyond the catheter 20 into the blood vessel of the patient.

In some embodiments, the connector 22 and the catheter adapter 12 may provide a straight pathway through which the instrument may travel and extend. In further detail, in some embodiments, the lumen of the connector 22 may be axially aligned with the lumen of the catheter adapter 12. In some embodiments, the connector 22 and connector support device 32 may act as an extension set, which is somewhat removed from the patient to prevent disruption of an insertion site of the catheter 20. However, in some embodiments, a length of the connector 22 and the catheter adapter 12 may not be overly extended, which may facilitate an increased reach of the instrument. In some embodiments, a blood collection or fluid infusion device may be coupled to the proximal end 28 of the connector 22.

In some embodiments, the connector support device 32 may include an H-shape, which may include four leg portions 34 and a bridge portion 36. In some embodiments, the H-shape may provide stabilization of the connector 22 and the catheter 20 by preventing rocking in a proximal-distal direction and/or from side to side. In some embodiments, the H-shape may provide stability while the instrument is being manipulated or inserted through the connector 22.

In some embodiments, the connector support device 32 may include an upper surface 38, which may contact and support the connector 22. In some embodiments, the body 24 and the side port 30 of the connector 22 may rest on the upper surface 38. In some embodiments, the connector support device 32 may include a bottom surface 40 configured to contact the skin of the patient.

In some embodiments, the connector support device 32 may include various stabilization features. In some embodiments, the connector support device 32 may include a ring 42, which may extend from the upper surface 38. In some embodiments, the body 24 of the connector 22 may extend through the ring 42. In some embodiments, the ring 42 may contact the connector 22 and hold the connector 22 snugly in place.

In some embodiments, the upper surface 38 may include a groove 44, which may be aligned with a longitudinal axis 46 of the connector 22. In some embodiments, the connector 22 may rest within the groove 44. In some embodiments, a thickness of the connector support device 32 at a proximal end of the groove 44 may be greater than a thickness of the connector support device 32 at a distal end of the groove 44 such that groove 44 may support the connector 22 at the insertion angle.

In some embodiments, the upper surface 38 of the connector support device 32 may include one or more protrusions 48, which may contact the side port 30. In some embodiments, the protrusions 48 may be disposed adjacent the side port 30 and may contact the side port 30 in response to movement of the side port 30 to stabilize the side port 30. In some embodiments, the protrusions 48 may be disposed proximal to the side port 30 and/or laterally to the ring 42, as illustrated in FIG. 1A, for example. In some embodiments, the protrusions 48 may be disposed distal to the side port 30.

In some embodiments, the connector support device 32 may include a first protrusion on a first side of the connector support device 32 and a second protrusion on a second side of the connector support device 32 opposite the first side, as illustrated, for example, in FIGS. 1A-1B. In these and other embodiments, the connector support device 32 may be compatible with the side port 30 extending from either side of the connector 22. It is understood that in some embodiments, the upper surface 38 may include a single protrusion 48. Also, in some embodiments, the protrusions 48 may be disposed on both sides of the groove 44 and/or the connector support device 32 to allow support of the side port 30 with the connector 22 in various orientations. Further, in some embodiments, the protrusions 48 may be disposed on a single side of the groove 44 and/or the connector support device 32.

In some embodiments, the catheter system 10 may be packaged with the connector support device 32 pre-attached, which may prevent assembly by the clinician. Thus, in some embodiments, the connector support device 32 may be coupled to the connector 22 prior to insertion of the catheter 20 and the introducer needle into the blood vessel of the patient. In some embodiments, coupling of the connector support device 32 to the connector 22 post-insertion by the clinician is avoided.

Figure 2A:
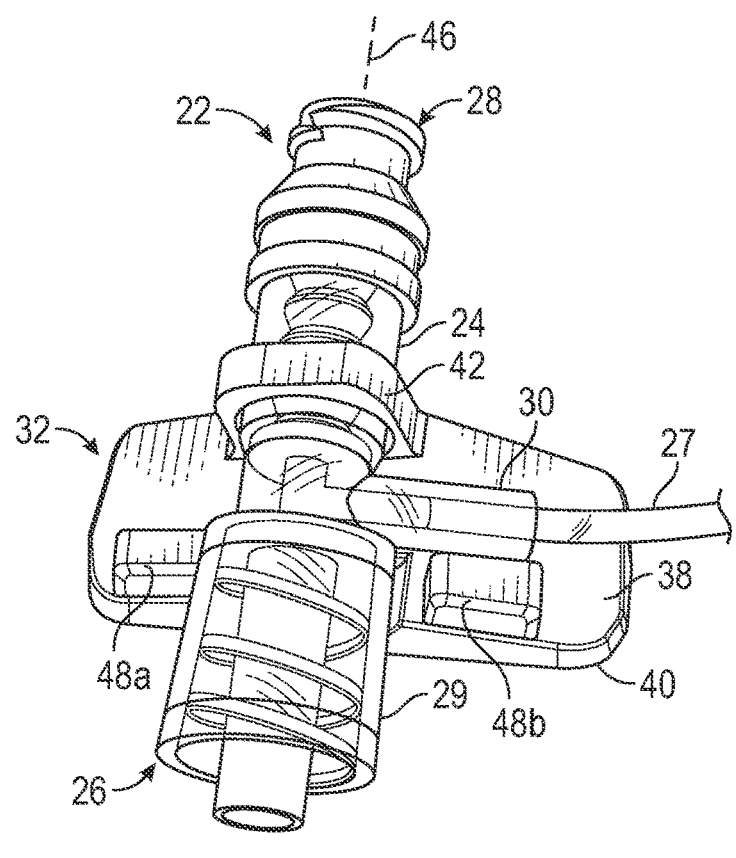
FIG. 2A is an upper perspective view of the connector and another example connector support device, according to some embodiments.
Figure 2B:
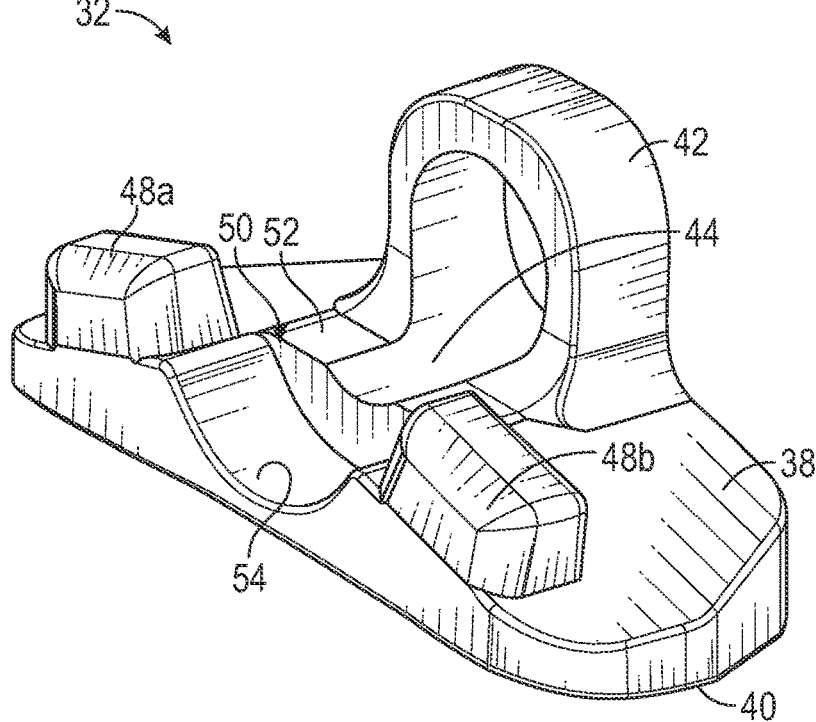
FIG. 2B is an upper perspective view of the connector support device of FIG. 2A, according to some embodiments.

Referring now to FIG. 2A-2B, in some embodiments, the connector support device 32 may include a stepped surface 50 forming an upper step 52 and a lower step 54. In some embodiments, the upper step 52 may include the groove 44. In some embodiments, the distal end 26 of the body 24 may include the luer adapter 29, which may rest on and/or within the lower step 54. In some embodiments, the lower step 54 may be curved. In some embodiments, the lower step 54 may be curved to match a cylindrical shape of the luer adapter 29. In some embodiments, a diameter of a curve of the lower step 54 may be greater than a diameter of a curve of the groove 44, which may reduce drag of the luer adapter 29 during assembly of the catheter system 10. In some embodiments, the luer adapter 29 may be disposed between a first protrusion 48a and a second protrusion 48b.

Figure 3A:
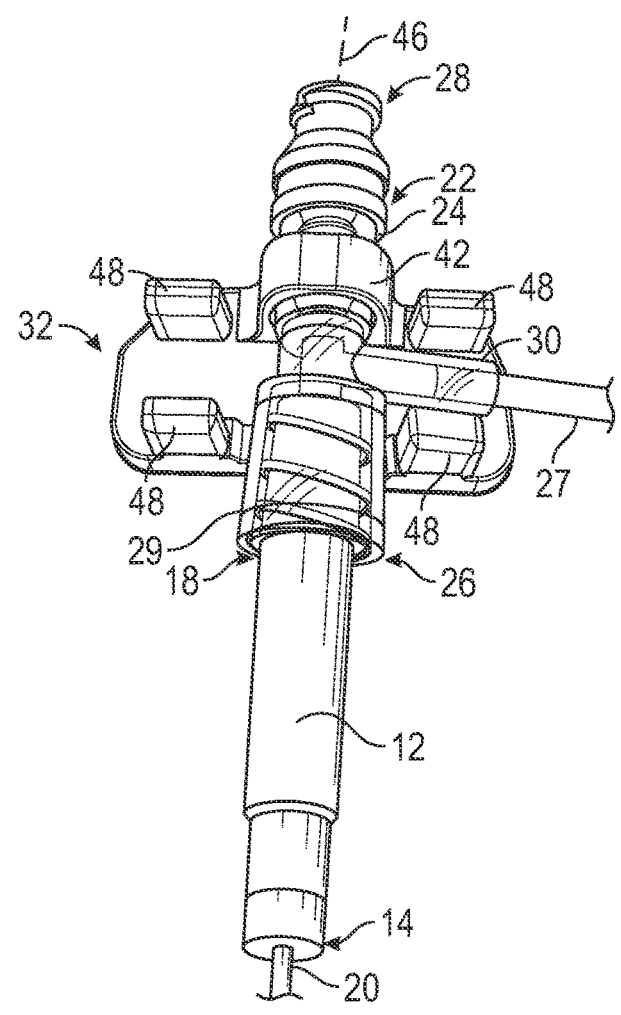
FIG. 3A is an upper perspective view of the connector and another example connector support device, according to some embodiments.
Figure 3B:
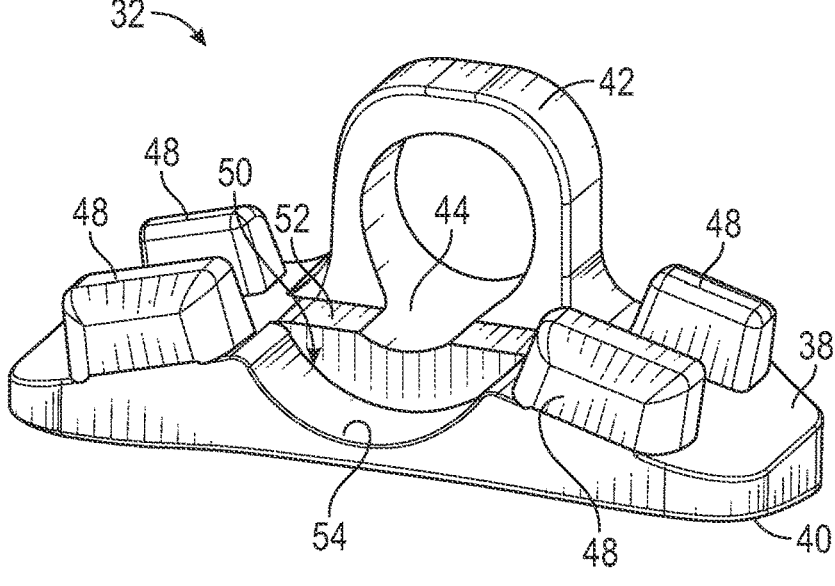
FIG. 3B is an upper perspective view of the connector support device of FIG. 3A, according to some embodiments.
Figure 4A:
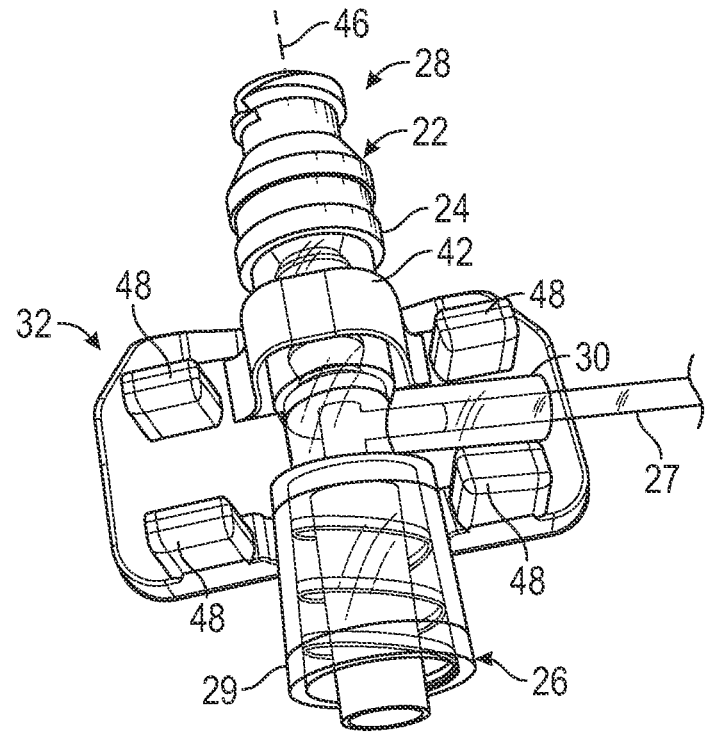
FIG. 4A is an upper perspective view of the connector and another example connector support device, according to some embodiments.
Figure 4B:
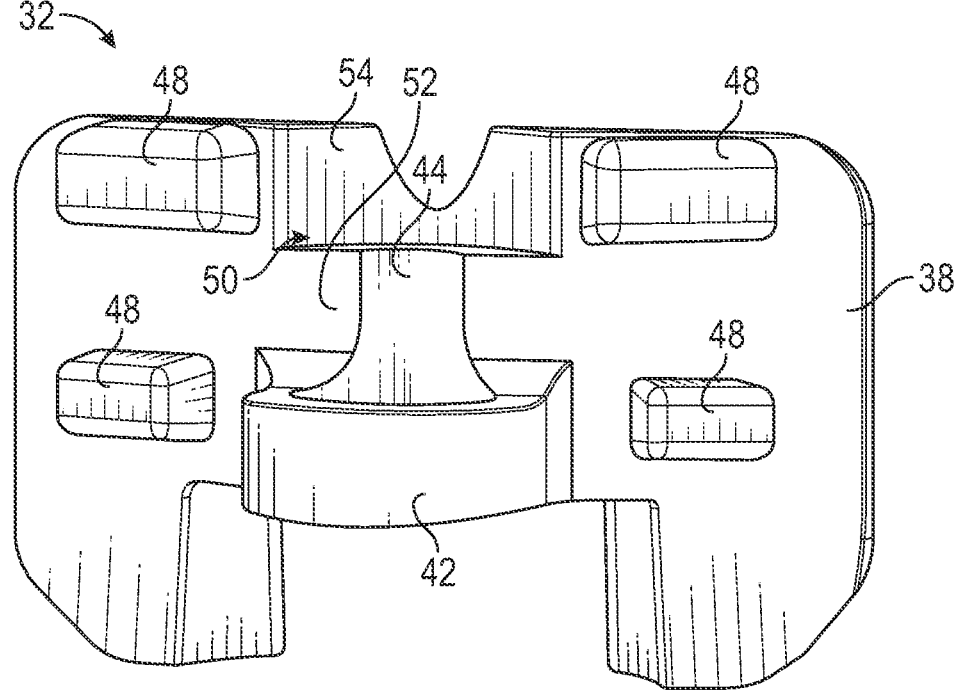
FIG. 4B is an upper perspective view of the connector support device of FIG. 4A, according to some embodiments.

Referring now to FIGS. 3A-4B, in some embodiments, the side port 30 may be disposed between a set of protrusions 48, as illustrated, for example, in FIGS. 3A and 4A. In some embodiments, the upper surface 38 of the connector support device 32 may include four of the protrusions 48.

Figure 5A:
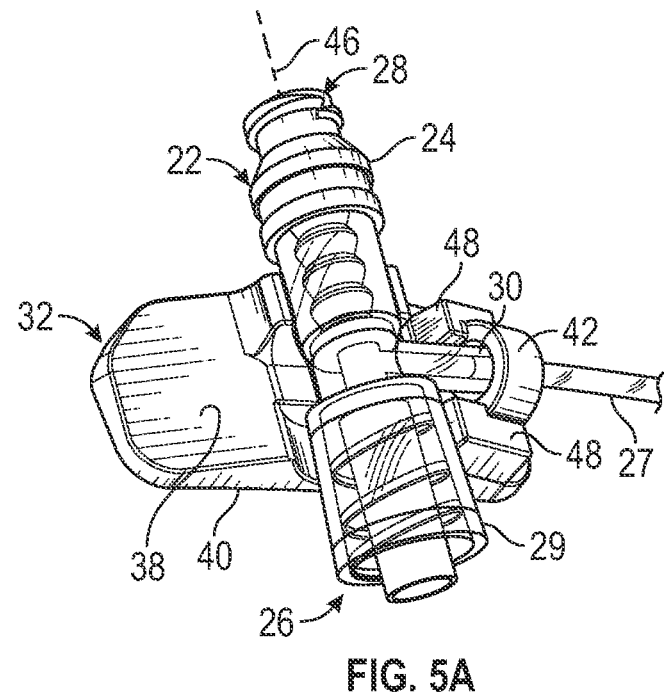
FIG. 5A is an upper perspective view of the connector and another example connector support device, according to some embodiments.
Figure 5B:
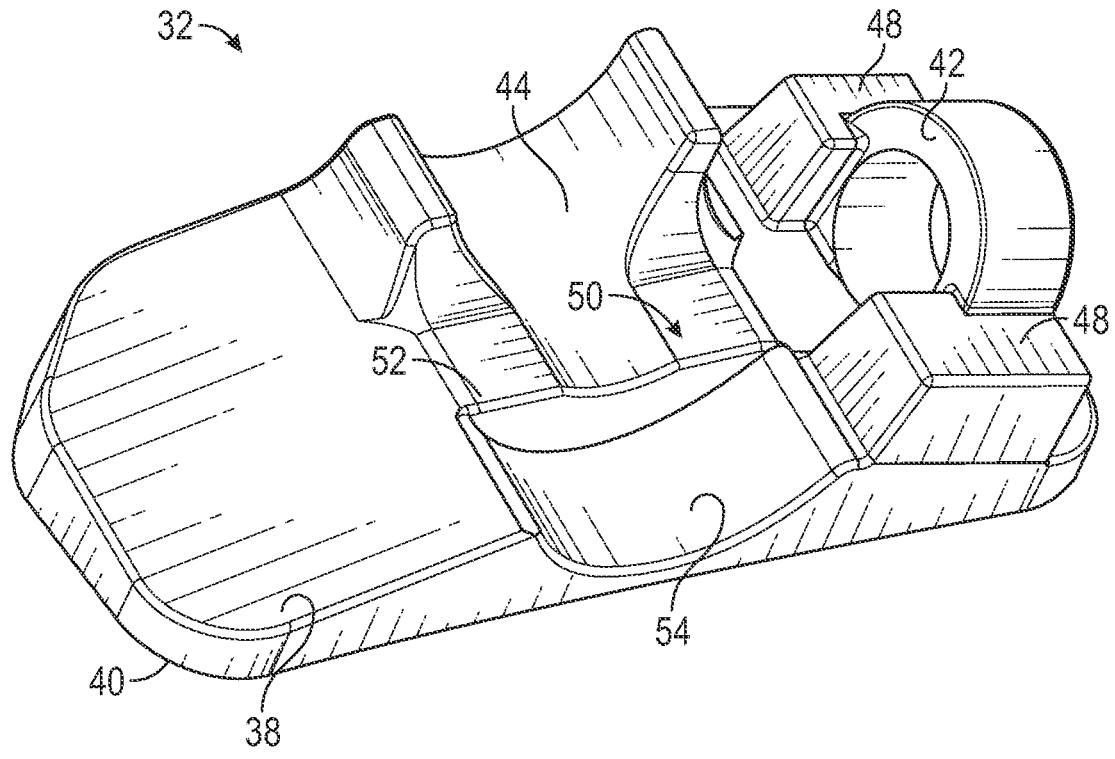
FIG. 5B is an upper perspective view of the connector support device of FIG. 5A, according to some embodiments.

Referring now to FIGS. 5A-5B, in some embodiments, the ring 42 may be oriented to receive the side port 30 of the connector 22, which may extend through the ring 42. In these embodiments, the ring 42 may be oriented generally perpendicular to the longitudinal axis 46 of the connector 22 and/or the groove 44. In some embodiments, the ring 42 may contact the side port 30 and hold the side port 30 snugly in place. In some embodiments, with placement of the ring 42 as illustrated in FIGS. 5A-5B, the connector 22 may be coupled to the catheter adapter 12 prior to coupling of the connector support device 32 to the connector 22.

Figure 6A:
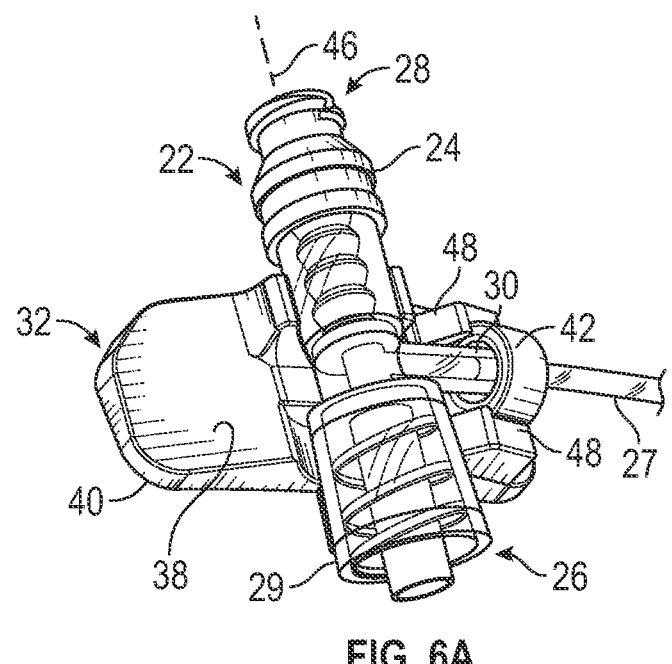
FIG. 6A is an upper perspective view of the connector and another example connector support device, according to some embodiments.
Figure 6B:
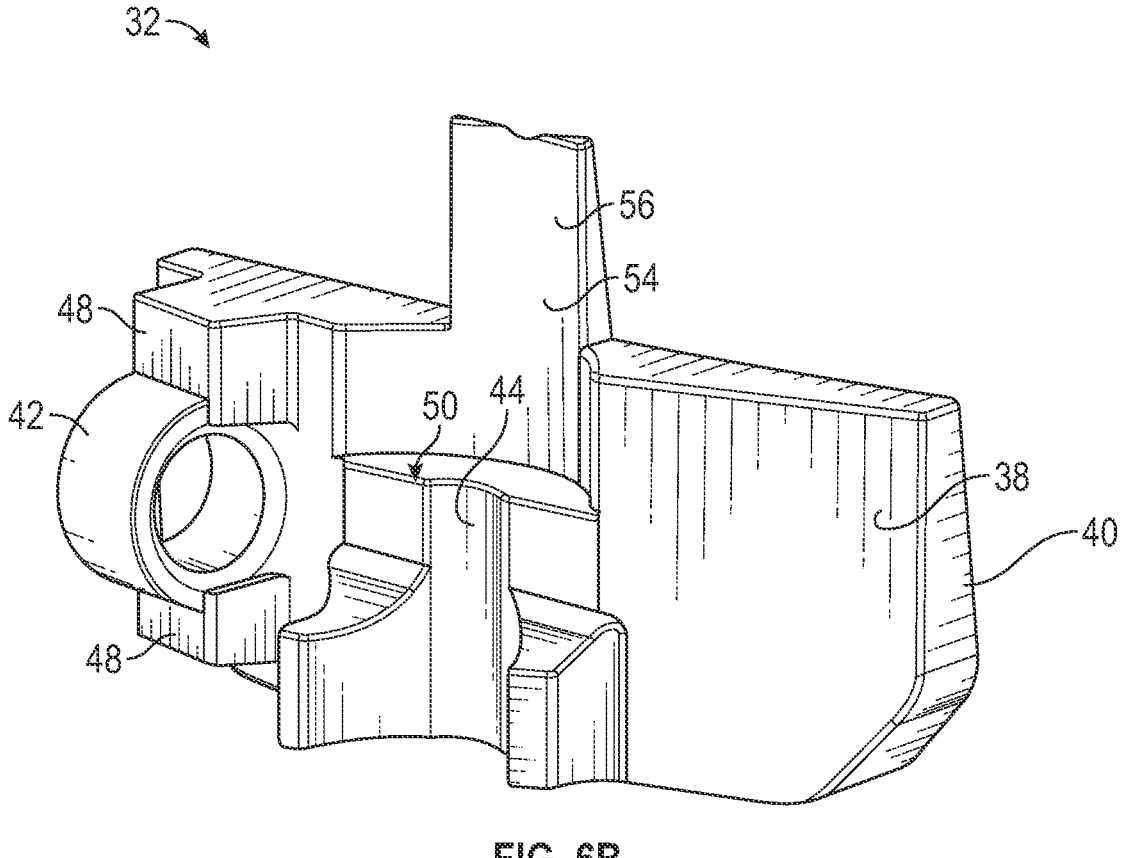
FIG. 6B is an upper perspective view of the connector support device of FIG. 6A, according to some embodiments.

Referring now to FIGS. 6A-6B, in some embodiments, the connector support device 32 may include an extension 56, which may extend distally from the lower step 54. In some embodiments, the luer adapter 29 may rest on the extension 56. In some embodiments, the extension 56 may improve patient comfort.

In some embodiments, at least a portion of the connector support device 32 may be constructed of a rigid material. In some embodiments, at least a portion of the connector support device 32, such as, for example, the extension 56, may be constructed of a soft, flexible material, which may conform to the skin of the patient.

Figure 7A:
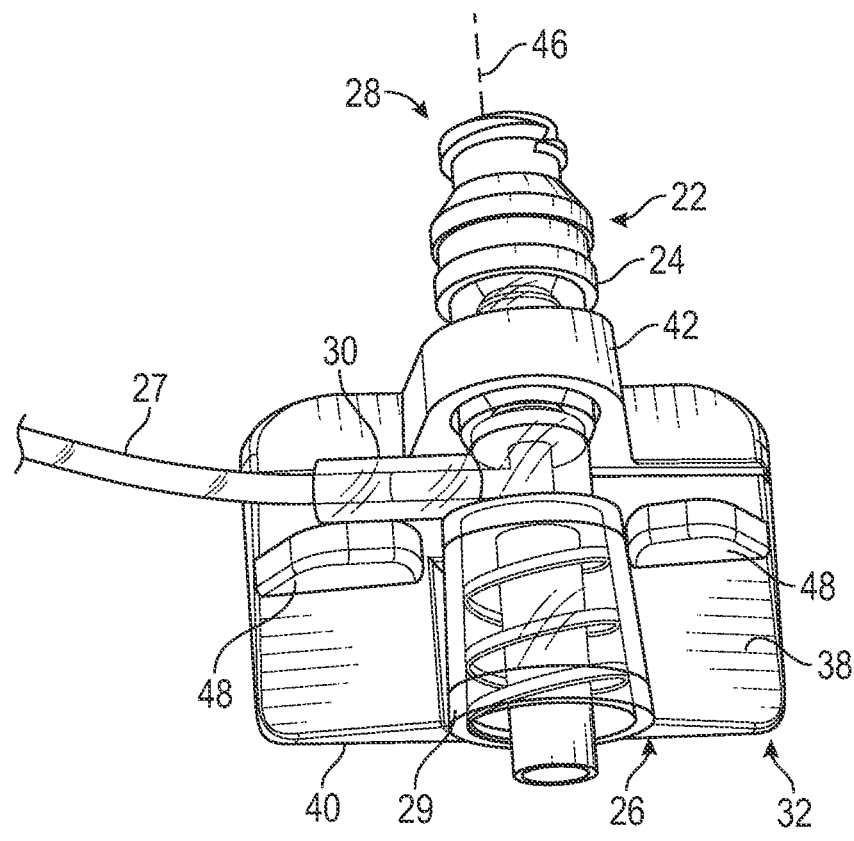
FIG. 7A is an upper perspective view of the connector and another example connector support device, illustrating the connector in a first position, according to some embodiments.
Figure 7B:
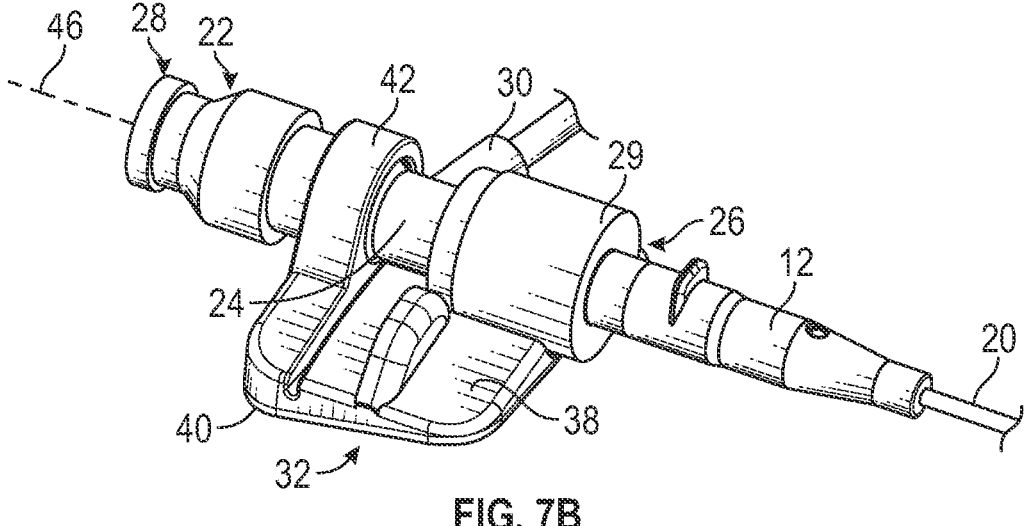
FIG. 7B is an upper perspective view of the connector and connector support device of FIG. 7A, illustrating the connector in a second position, according to some embodiments.

Referring now to FIGS. 7A-7B, in some embodiments, the protrusions 48 may be disposed distal to the side port 30. In some embodiments, the side port 30 may be disposed between the ring 42 and a particular protrusion 48.

Figure 8A:
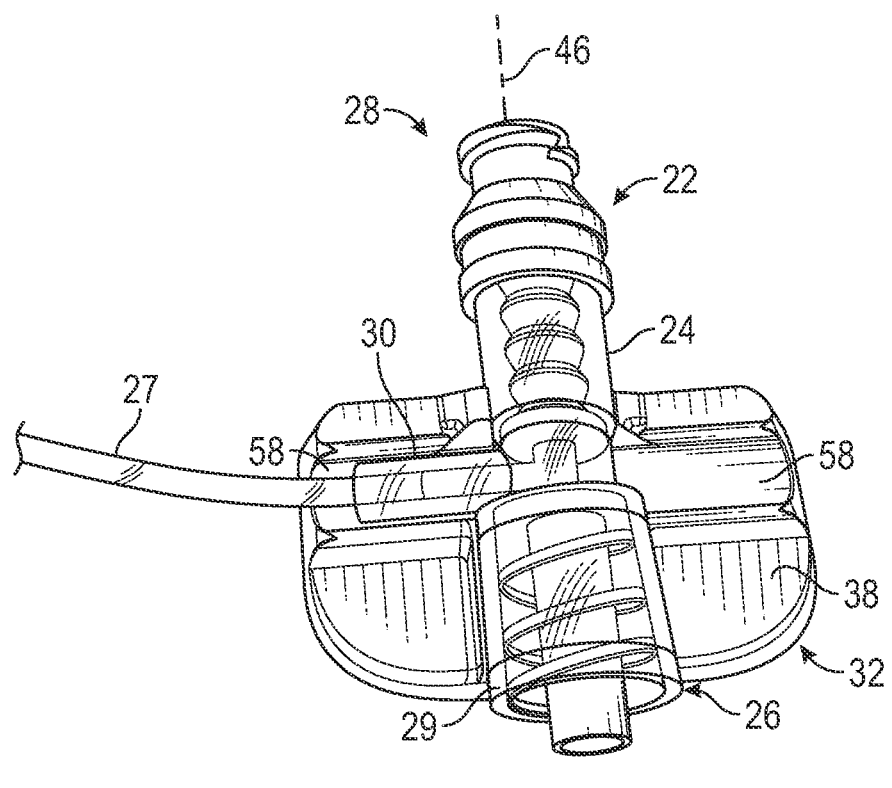
FIG. 8A is an upper perspective view of the connector and another example connector support device, illustrating the connector in a first position, according to some embodiments.
Figure 8B:
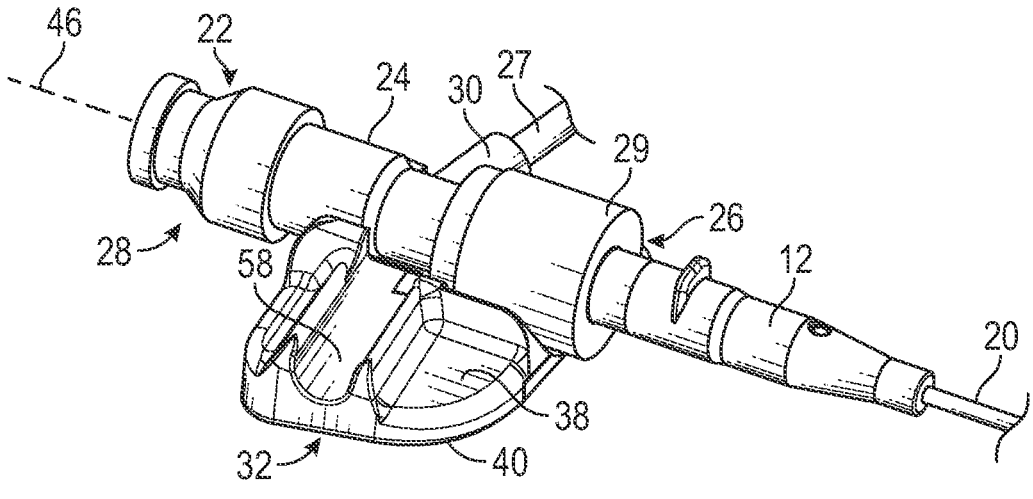
FIG. 8B is an upper perspective view of the connector and connector support device of FIG. 8A, illustrating the connector in a second position, according to some embodiments.

Referring now to FIGS. 8A-8B, in some embodiments, the upper surface 38 may include one or more other grooves 58, which may be generally perpendicular to the longitudinal axis 46 of the connector 22. In some embodiments, the side port 30 of the connector 22 may be configured to rest within the other grooves 58.

Figure 9A:
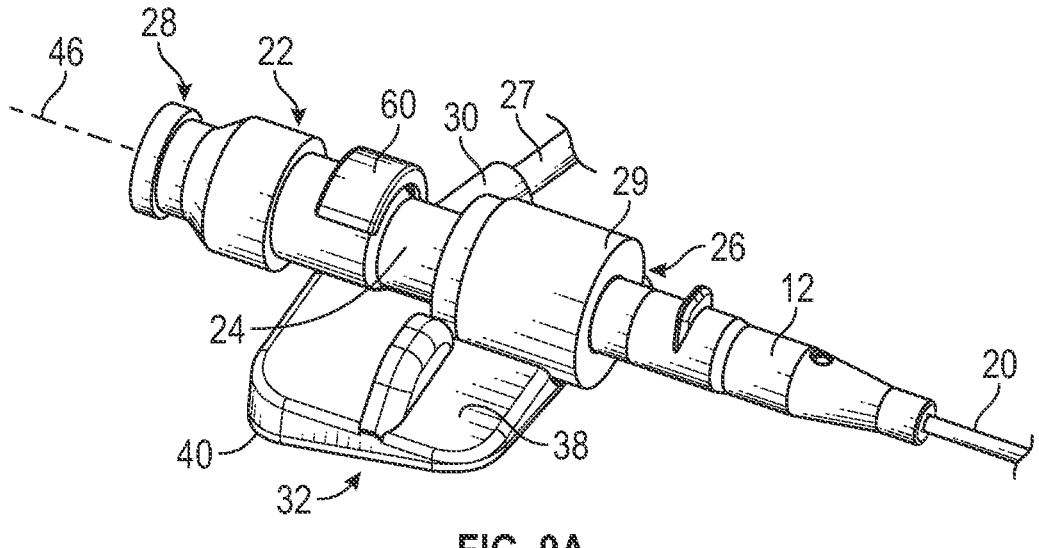
FIG. 9A is an upper perspective view of the connector and another example connector support device, illustrating the connector in a first position, according to some embodiments.
Figure 9B:
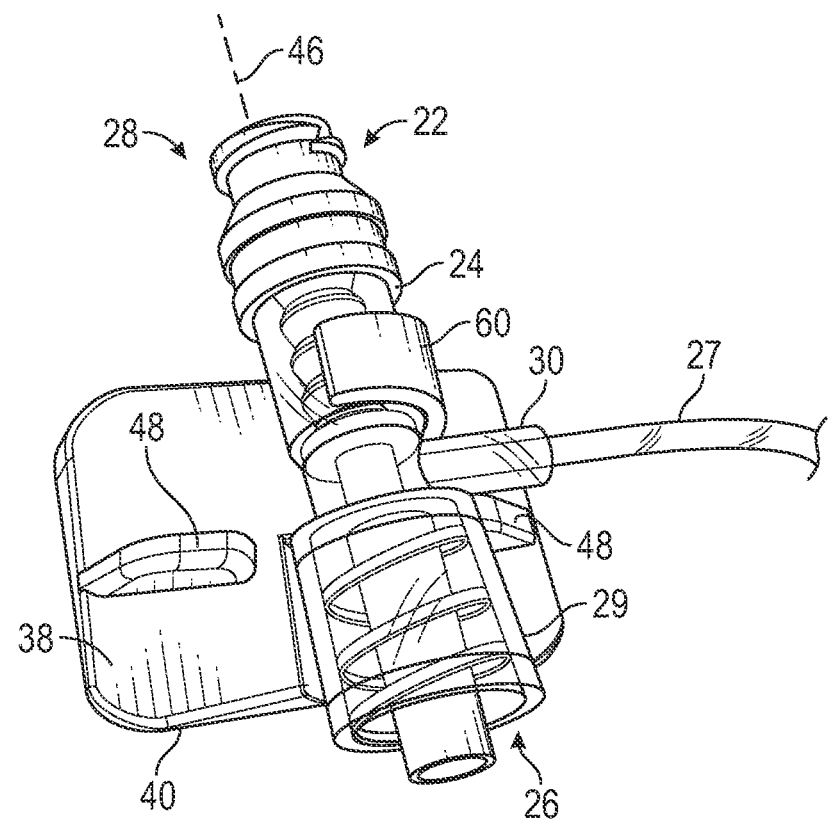
FIG. 9B is an upper perspective view of the connector and connector support device of FIG. 9A, illustrating the connector in a second position, according to some embodiments.
Figure 9C:
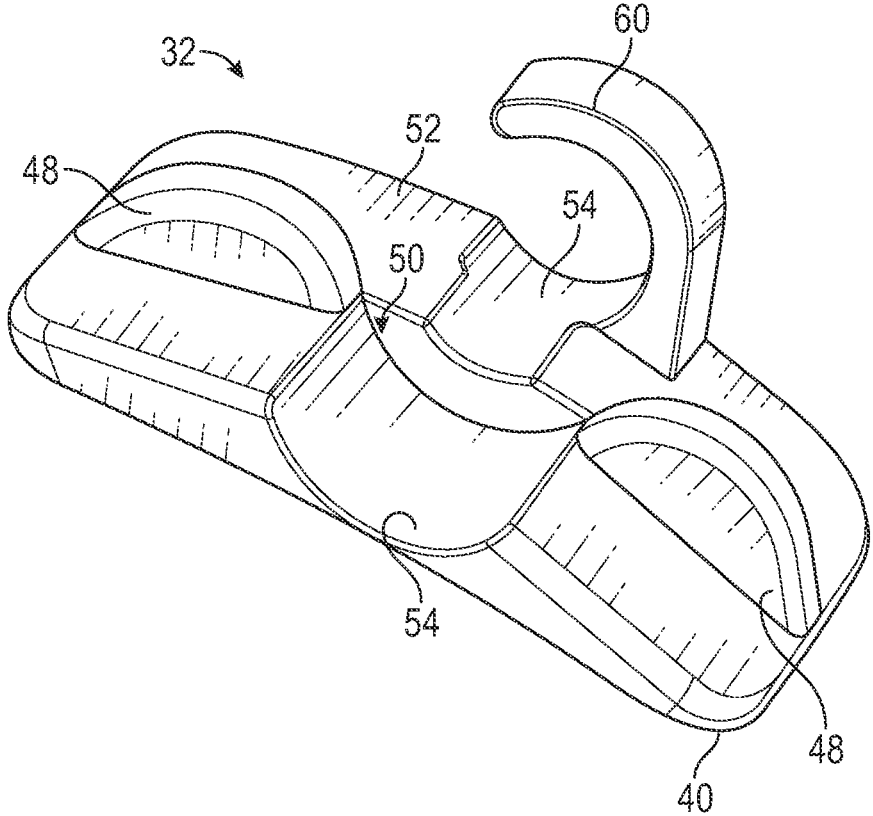
FIG. 9C is an upper perspective view of the connector support device of FIG. 9A, according to some embodiments.
Figure 10A:
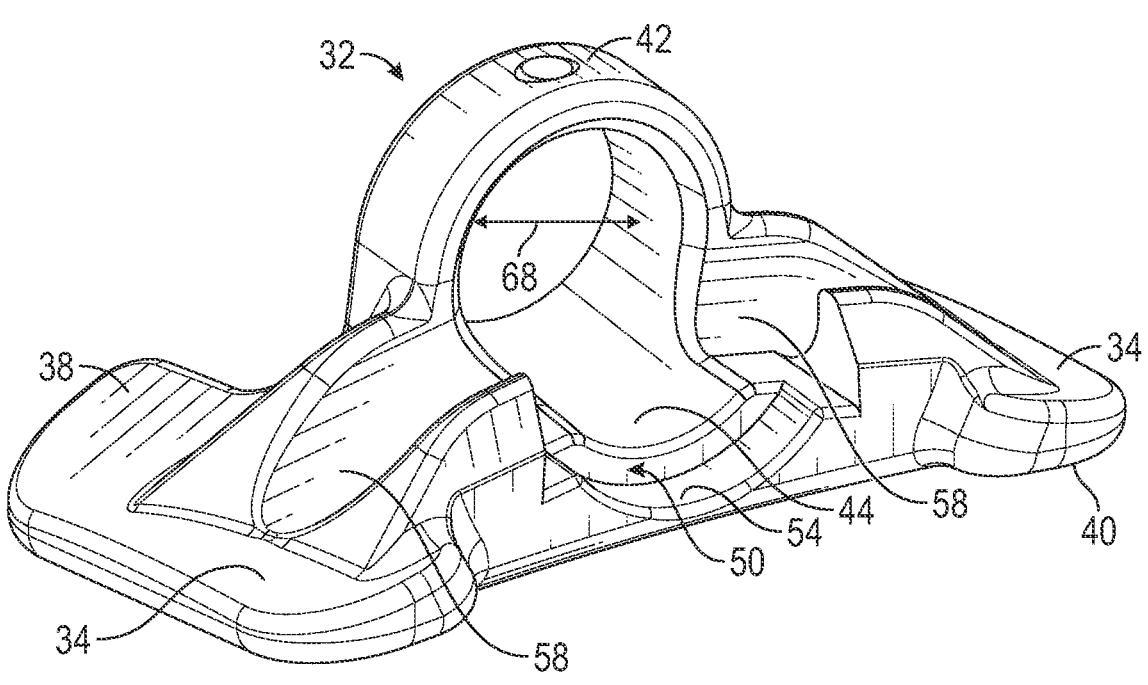
FIG. 10A is an upper perspective view of another example connector support device, according to some embodiments.
Figure 10B:
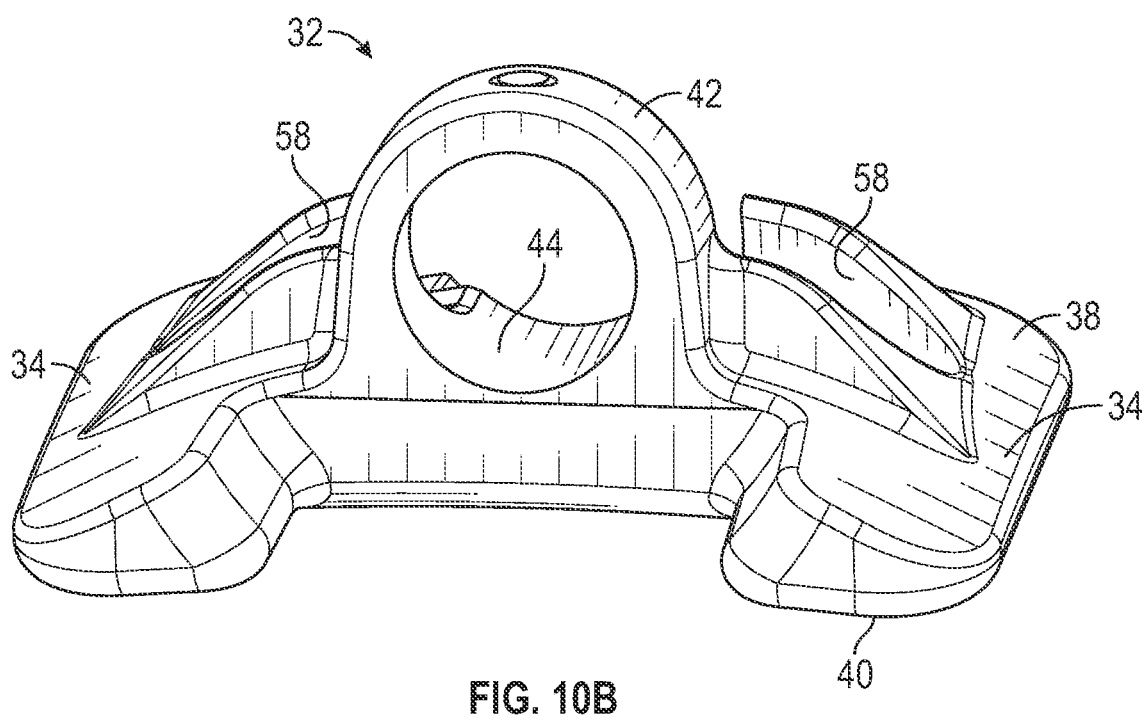
FIG. 10B is another upper perspective view of the connector support device of FIG. 10A, according to some embodiments.
Figure 10C:
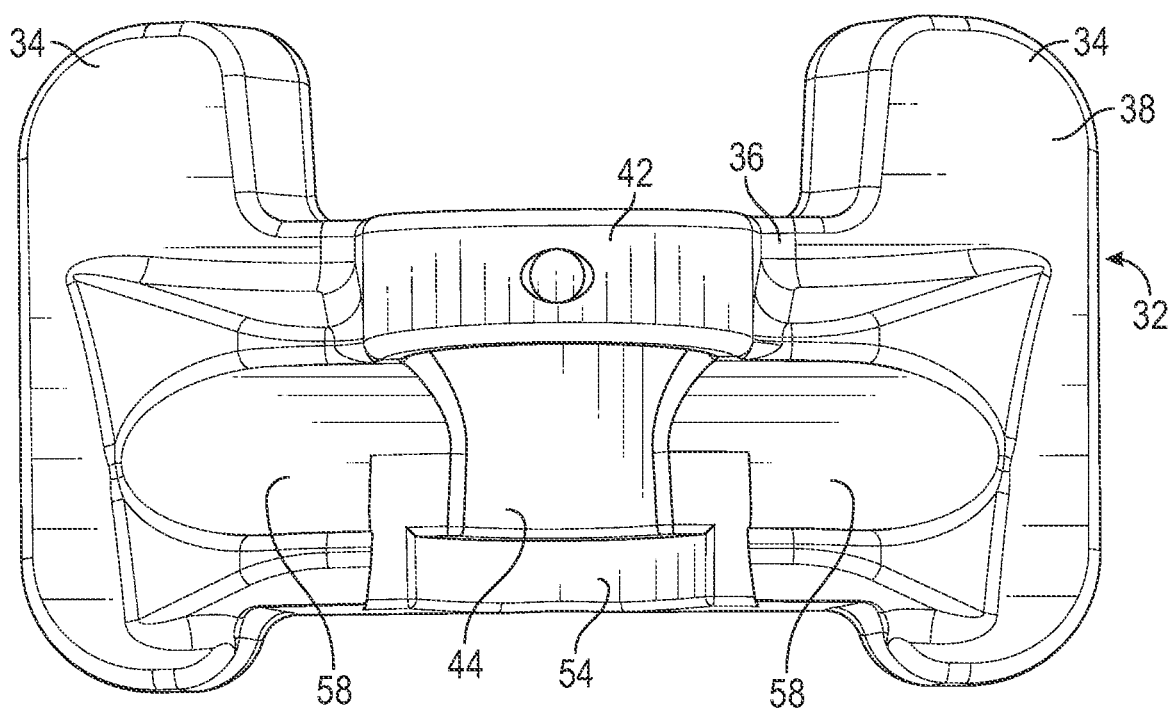
FIG. 10C is a top view of the connector support device of FIG. 10A, according to some embodiments.
Figure 10D:
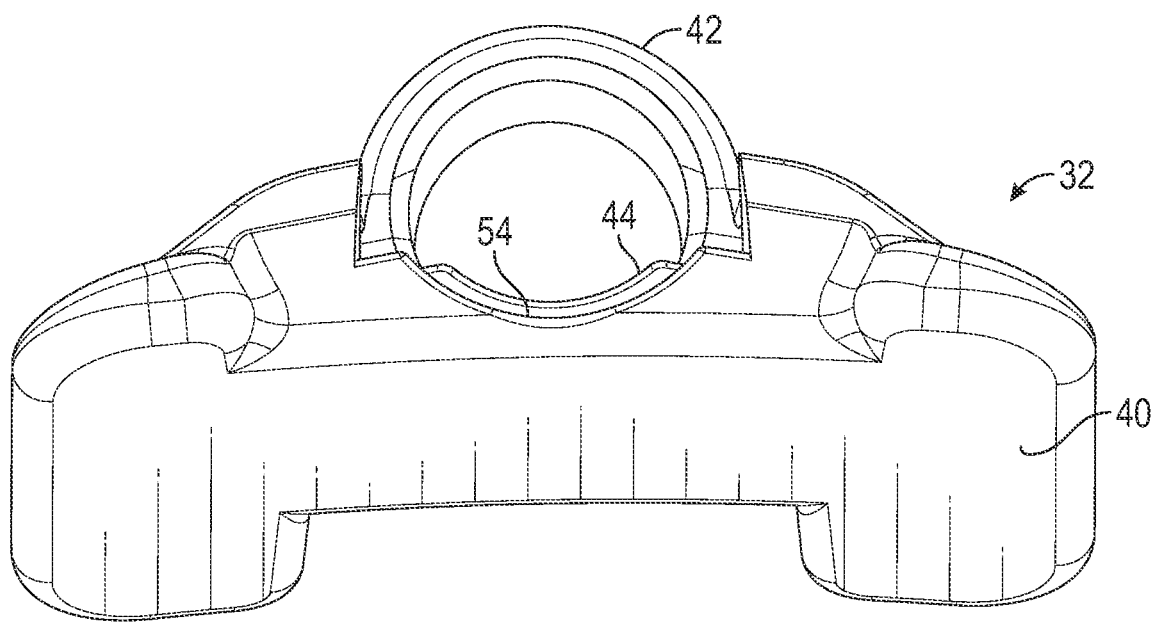
FIG. 10D is a lower perspective view of the connector support device of FIG. 10A, according to some embodiments.

Referring now to FIGS. 9A-9B, in some embodiments, the connector support device 32 may include a partial ring 60, which may extend from the upper surface 38. In some embodiments, the ring 42 described with respect to one or more of the previous figures may be substituted with the partial ring 60. In some embodiments, the body 24 of the connector 22 may extend through the partial ring 60. In some embodiments, the partial ring 60 may contact the connector 22 and hold the connector 22 snugly in place.

In some embodiments, the connector support device 32 may be pre-attached to the connector 22 prior to shipping and/or prior to insertion of the catheter system 10 into the vasculature of the patient. In some embodiments, the partial ring 60 may facilitate removal of the connector support device 32, which may be reused.

In some embodiments, the connector support device 32 may be coupled to the proximal end 18 of the catheter adapter 12. In some embodiments, the connector support device 32 may be monolithically formed as a single unit with the proximal end 18 of the catheter adapter 12.

In some embodiments, the bottom surface 40 of the connector support device 32 may include an adhesive, which may facilitate attachment to the skin of the patient. In some embodiments, an adhesive may be disposed between the connector 22 and the connector support device 32. In these and other embodiments, the connector 22 may be secured to the connector support device 32 via magnets, a tether, or any other suitable coupling mechanism.

In some embodiments, another extension tube may be disposed between the connector 22 and the catheter adapter 12. In some embodiments, the other extension tube may be stiffer than the extension tube 27 to facilitate an axial pathway for insertion of the instrument through the other extension tube. In some embodiments, a needleless connector may be disposed between the connector 22 and the catheter adapter 12. In some embodiments, the needleless connector may be monolithically formed as a single unit with the catheter adapter 12 or removable from the catheter adapter 12.

In some embodiments, the catheter system 10 may include any suitable needle safety mechanism, including, for example, a passive or active needle safety mechanism. In some embodiments, the catheter system 10 may not include a needle safety mechanism. In some embodiments, the introducer needle and/or the needle safety mechanism may be removed prior to coupling of the connector 22 to the catheter adapter 12.

Referring now to FIGS. 10A-11F, in some embodiments, the connector support device 32 may include the bottom surface 40 configured to contact the skin of the patient. In some embodiments, the bottom surface 40 may be arc shaped, which may facilitate stabilization on a curvature of the skin of the patient.

In some embodiments, the upper surface 38 may include the grooves 58, which may be generally perpendicular to the longitudinal axis 46 of the connector 22 and/or a central axis of the connector support device 32 extending in a distal-proximal direction. In some embodiments, the side port 30 of the connector 22 may be configured to rest within the other grooves 58. In some embodiments, the grooves 58 may be proximate and extend from the ring 42, which may provide support to walls of the grooves 58 and/or alignment of the connector 22 within the connector support device 32.

In some embodiments, the connector support device 32 may include the stepped surface 50 forming the upper step 52 and the lower step 54. In some embodiments, the upper step 52 may include the groove 44. In some embodiments, the distal end 26 of the body 24 may include the luer adapter 29, which may rest on and/or within the lower step 54. In some embodiments, the lower step 54 may be curved or arc-shaped. In some embodiments, the lower step 54 may be curved to match the cylindrical shape of the luer adapter 29.

Figure 11A:
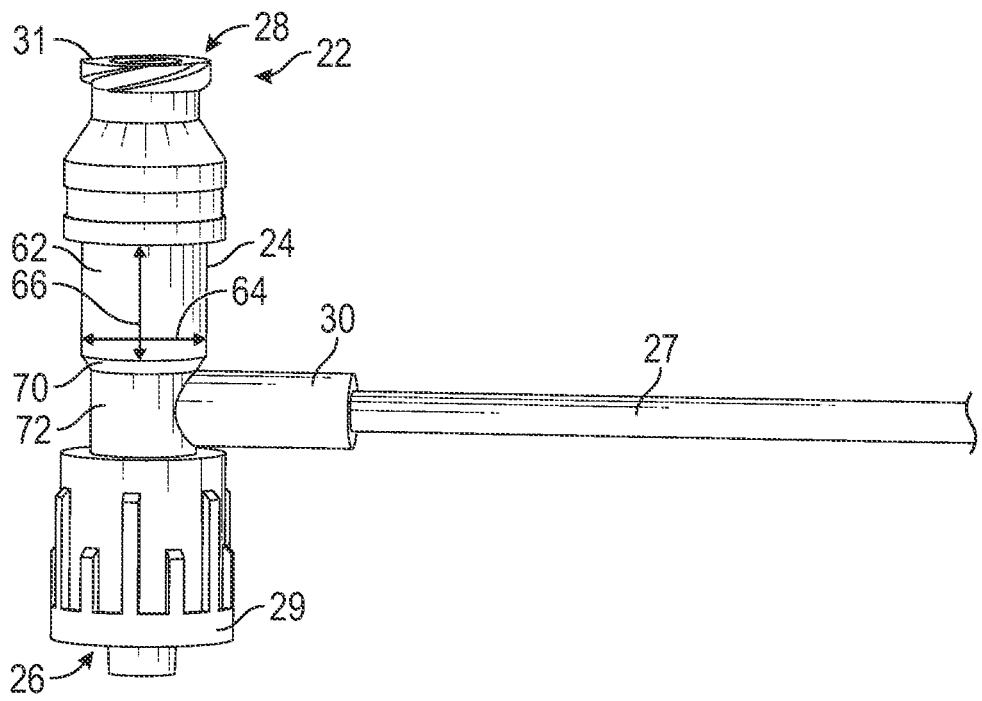
FIG. 11A is a top view of an example connector, according to some embodiments.
Figure 11B:
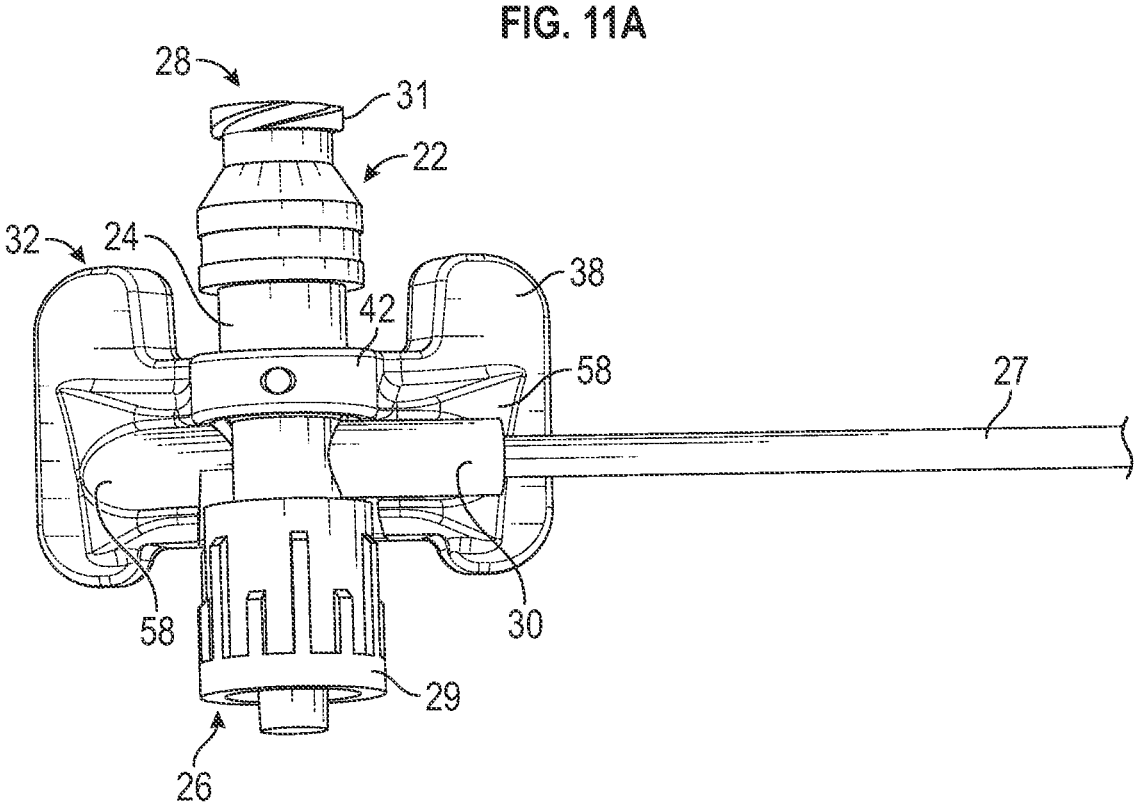
FIG. 11B is a top view of another example catheter system, illustrating the connector support device of FIG. 10A and the connector of FIG. 11A, according to some embodiments.
Figure 11C:
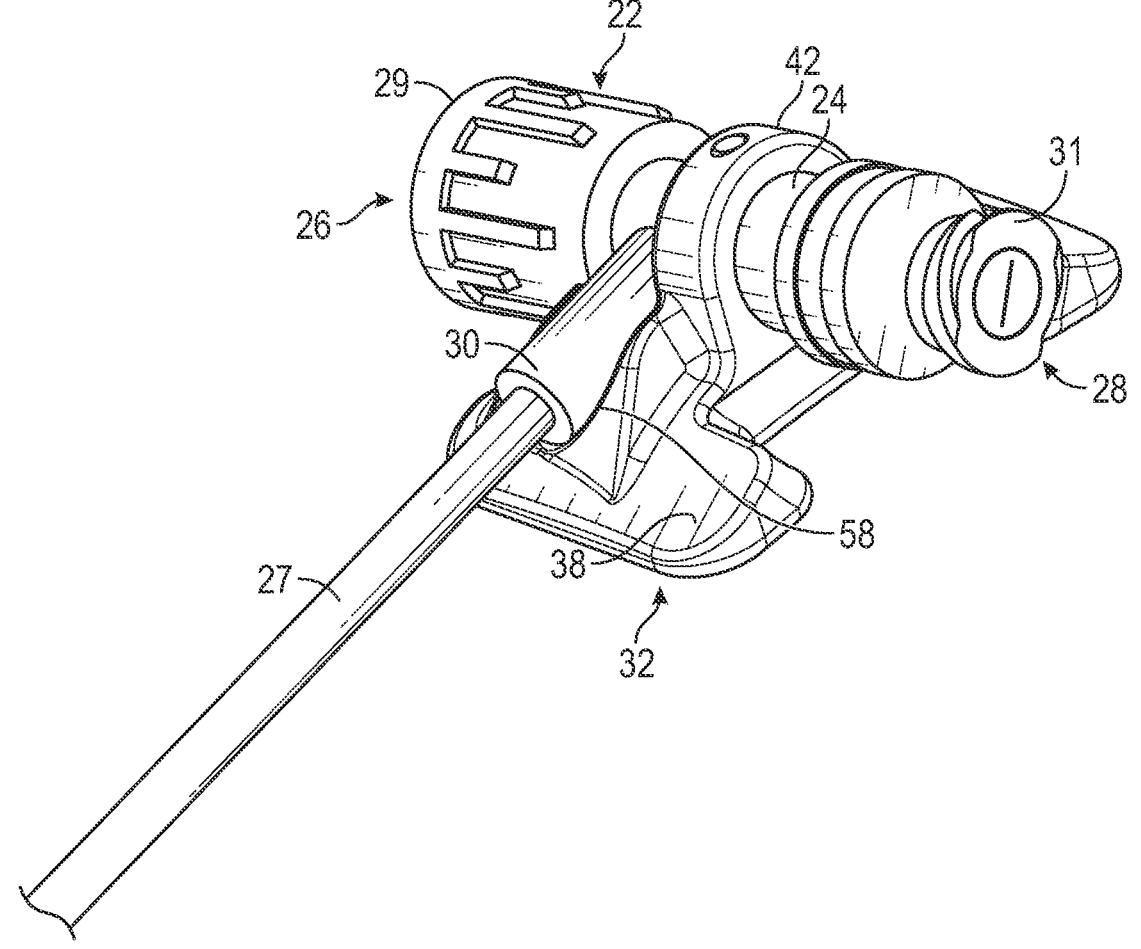
FIG. 11C is an upper perspective view of the catheter system of FIG. 11B, according to some embodiments.
Figure 11D:
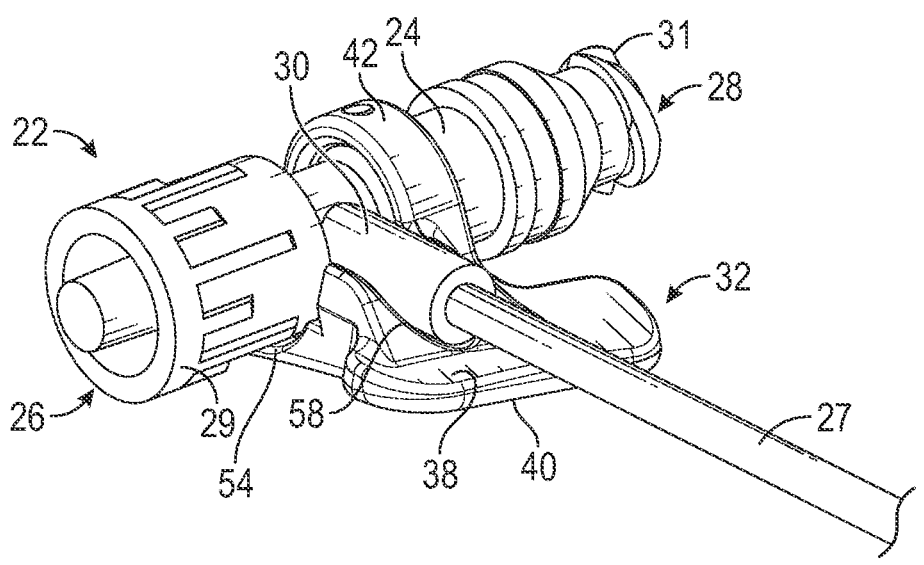
FIG. 11D is another upper perspective view of the catheter system of FIG. 11B, according to some embodiments.
Figure 11E:
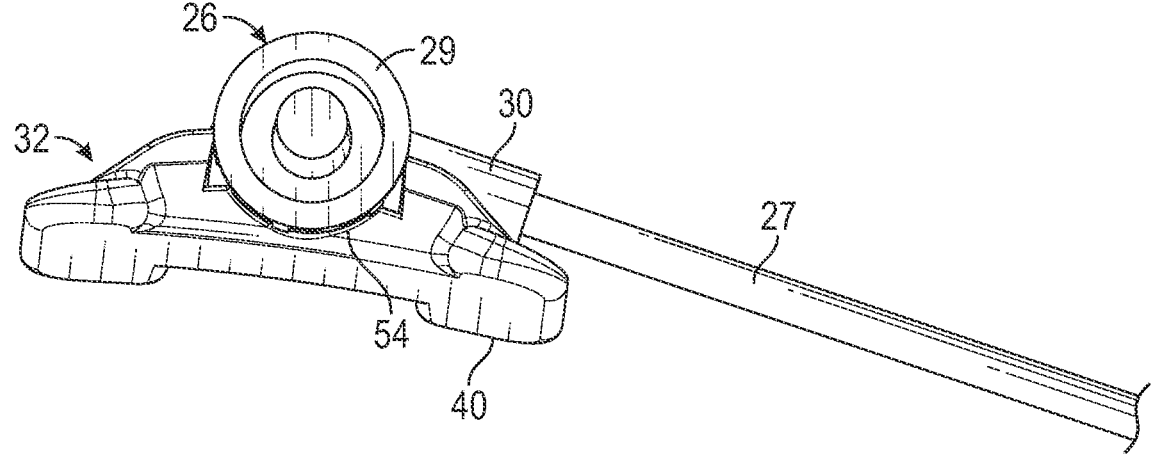
FIG. 11E is a distal end view of the catheter system of FIG. 11B, according to some embodiments.
Figure 11F:
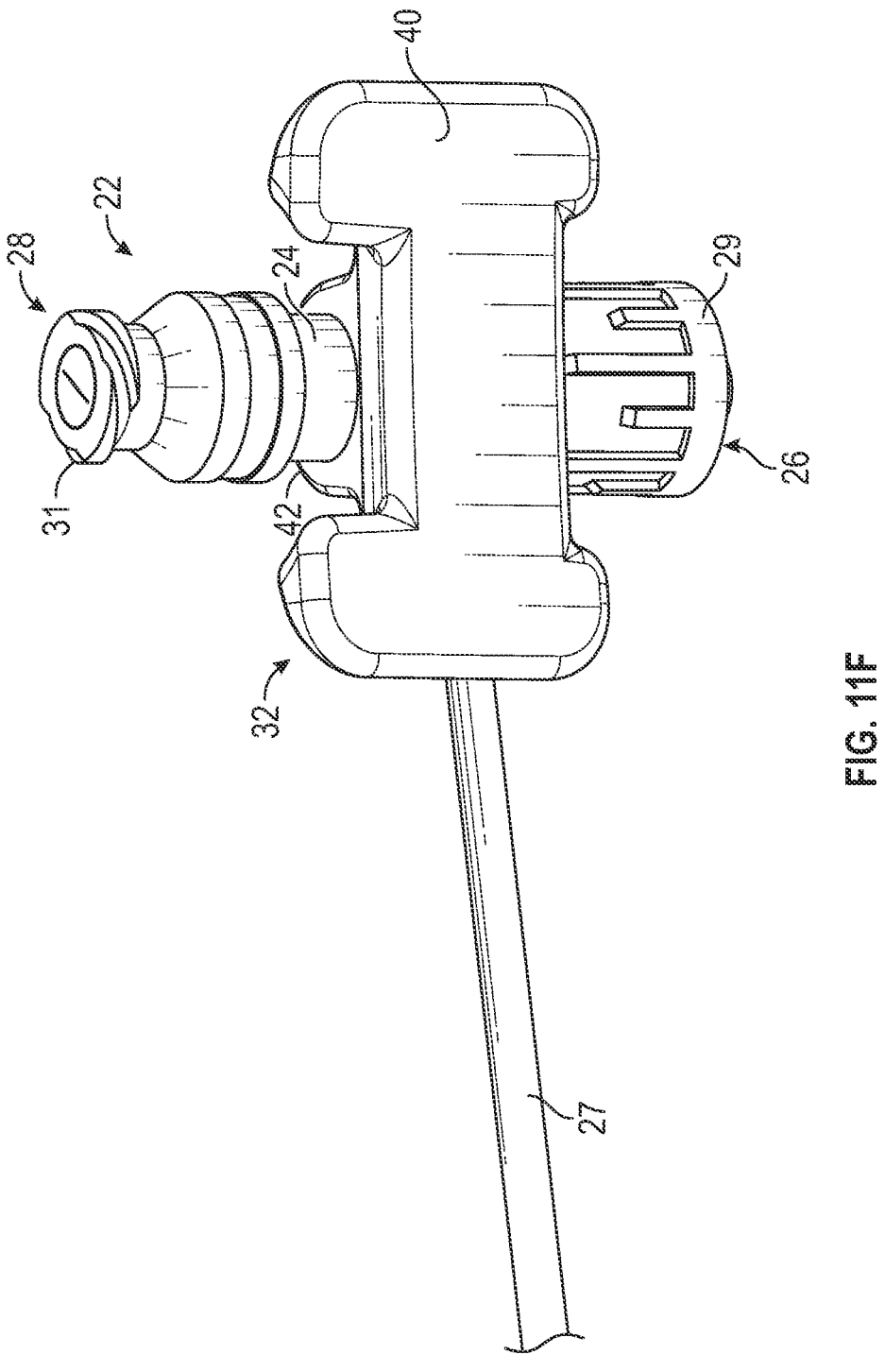
FIG. 11F is a lower perspective view of the catheter system of FIG. 11B, according to some embodiments.

As illustrated in FIG. 11A, in some embodiments, the connector 22 may include the body 24, which may include a distal end 26 and a proximal end 28. In some embodiments, the connector 22 may include a first middle portion 62, which may include an outer diameter 64. In some embodiments, the outer diameter 64 may be constant along an entirety of a length 66 of the first middle portion 62. In some embodiments, the outer diameter 64 may be equal to or slightly less than an inner diameter 68 of the ring 42. In some embodiments, all or a portion of an outer circumference of the first middle portion 62 may contact an inner circumference of the ring 42, which may facilitate support of the first middle portion 62.

In some embodiments, the first middle portion 62 may be proximate a transition surface 70, which may be distal to the first middle portion 62. In some embodiments, the transition surface 70 may be tapered or stepped. In some embodiments, the transition surface 70 may be proximate a second middle portion 72, from which the side port 30 may extend. In some embodiments, the second middle portion 72 may be distal to the transition surface 70 and proximal to the luer adapter 29. In some embodiments, the second middle portion 72 may not contact the groove 44, which may decrease friction between the connector 22 and the connector support device 52. In some embodiments, the second middle portion 72 may contact the groove 44. In some embodiments, the first middle portion 62 and/or the second middle portion 72 may be cylindrical.

In some embodiments, the connector 22 may be integrally formed with the connector support device 52. In some embodiments, the connector 22 and the connector support device 52 may be monolithically formed as a single unit. As mentioned, it should be understood that the embodiments may be combined. Thus, the connector support device 52 of FIGS. 10-11 may be similar or identical to one or more of the connector support devices 52 discussed with respect to FIGS. 1-9 in terms of one or more included features and/or operation.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A connector support device to support a connector coupled to a catheter assembly, the connector support device comprising:

a body having a symmetrical H-shape formed by a bridge portion and a plurality of legs, the plurality of legs including opposing left and right distal legs that extend distally from the bridge portion to a distalmost end of the body and opposing left and right proximal legs that extend proximally from the bridge portion to a proximal-most end of the body, the bridge portion and the plurality of legs having a bottom surface and an upper surface, the bottom surface being configured to contact skin of a patient, the upper surface being angled relative to the bottom surface such that a thickness of the body, including the bridge portion and the plurality of legs, increases linearly from the distalmost end of the body to the proximal-most end of the body, wherein the body has a plane of symmetry that extends between the left distal and proximal legs and the right distal and proximal legs and wherein a portion of the upper surface that lies in the plane of symmetry is oriented at a first angle relative to a portion of the bottom surface that lies in the plane of symmetry;

a ring or a partial ring extending upwardly from the upper surface, wherein the ring or the partial ring extends across the plane of symmetry, wherein the ring or the partial ring forms an open space that extends through a proximal side and a distal side of the ring or partial ring, wherein a longitudinal axis of the ring or the partial ring extends within the plane of symmetry and is oriented at the first angle, the open space being configured to receive the connector to thereby cause the connector to be oriented at the first angle;

a groove in the upper surface distal to the ring or partial ring; and a protrusion that extends upwardly from the upper surface, the protrusion being positioned to the left or right of the plane of symmetry, the protrusion having a distal face that is perpendicular to the plane of symmetry, the distal face being configured to contact a side port of the connector when the connector is supported in the groove and extends through the open space.

2. The connector support device of claim 1, wherein the upper surface comprises a set of protrusions including the protrusion and another protrusion, wherein the other protrusion comprises another distal face that is perpendicular to the plane of symmetry.

3. The connector support device of claim 1, wherein the distal face of the protrusion is configured to contact a proximal side of the side port.

* * * * *